(12) United States Patent
Kimm et al.

(10) Patent No.: US 9,089,657 B2
(45) Date of Patent: Jul. 28, 2015

(54) METHODS AND SYSTEMS FOR GATING USER INITIATED INCREASES IN OXYGEN CONCENTRATION DURING VENTILATION

(75) Inventors: Gardner Kimm, Carlsbad, CA (US); Dan Graboi, Encinitas, CA (US)

(73) Assignee: Covidien LP, Mansfield, MA (US)

( * ) Notice: Subject to any disclaimer, the term of this patent is extended or adjusted under 35 U.S.C. 154(b) by 940 days.

(21) Appl. No.: 13/271,680

(22) Filed: Oct. 31, 2011

(65) Prior Publication Data

US 2013/0104896 A1    May 2, 2013

(51) Int. Cl.
*A61M 16/00* (2006.01)
*A61M 16/12* (2006.01)
*A61M 16/10* (2006.01)

(52) U.S. Cl.
CPC ............. *A61M 16/00* (2013.01); *A61M 16/105* (2013.01); *A61M 16/12* (2013.01); *A61M 2016/0027* (2013.01); *A61M 2202/0208* (2013.01); *A61M 2205/505* (2013.01); *A61M 2230/435* (2013.01)

(58) Field of Classification Search
CPC ............ A61M 16/00; A61M 16/0003; A61M 16/0051; A61M 16/10–16/103; A61M 16/12
See application file for complete search history.

(56) References Cited

U.S. PATENT DOCUMENTS

| | | |
|---|---|---|
| 269,929 A | 1/1883 | Hanlon |
| 3,805,780 A | 4/1974 | Cramer et al. |
| 3,941,124 A | 3/1976 | Rodewald et al. |
| 4,056,098 A | 11/1977 | Michel et al. |
| 4,141,354 A | 2/1979 | Ismach |
| 4,211,221 A | 7/1980 | Schwanbom et al. |
| 4,211,239 A | 7/1980 | Raemer et al. |
| 4,305,388 A | 12/1981 | Brisson |
| 4,340,044 A | 7/1982 | Levy et al. |
| 4,592,349 A | 6/1986 | Bird |
| 4,651,729 A | 3/1987 | Rae |
| 4,752,089 A | 6/1988 | Carter |
| 4,889,116 A | 12/1989 | Taube |
| 4,921,642 A | 5/1990 | LaTorraca |
| 4,939,647 A | 7/1990 | Clough et al. |
| 4,954,799 A | 9/1990 | Kumar |
| 4,971,052 A | 11/1990 | Edwards |
| 4,986,268 A | 1/1991 | Tehrani |
| 5,007,420 A | 4/1991 | Bird |
| 5,020,516 A | 6/1991 | Biondi et al. |
| 5,057,822 A | 10/1991 | Hoffman |
| 5,072,737 A | 12/1991 | Goulding |

(Continued)

FOREIGN PATENT DOCUMENTS

| | | |
|---|---|---|
| WO | WO2004000114 | 12/2003 |
| WO | WO2006121372 | 11/2006 |

(Continued)

OTHER PUBLICATIONS

7200 Series Ventilator, Options, and Accessories: Operator's Manual. Nellcor Puritan Bennett, Part No. 22300 A, Sep. 1990, pp. 1-196.

(Continued)

*Primary Examiner* — Rachel Young

(57) ABSTRACT

This disclosure describes systems and methods for ventilating a patient. The disclosure describes novel systems and methods for preventing and/or reducing the likelihood of a patient from receiving too much oxygen during a selected limited increase in oxygen concentration for a set period of time.

22 Claims, 3 Drawing Sheets

(56) References Cited

U.S. PATENT DOCUMENTS

| | | |
|---|---|---|
| 5,092,326 A | 3/1992 | Winn et al. |
| 5,094,235 A | 3/1992 | Westenskow et al. |
| 5,116,088 A | 5/1992 | Bird |
| 5,150,291 A | 9/1992 | Cummings et al. |
| 5,161,525 A | 11/1992 | Kimm et al. |
| 5,237,987 A | 8/1993 | Anderson et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,315,989 A | 5/1994 | Tobia |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,365,922 A | 11/1994 | Raemer |
| 5,368,019 A | 11/1994 | LaTorraca |
| 5,377,671 A | 1/1995 | Biondi et al. |
| 5,383,449 A | 1/1995 | Forare et al. |
| 5,385,142 A | 1/1995 | Brady et al. |
| 5,388,575 A | 2/1995 | Taube |
| 5,390,666 A | 2/1995 | Kimm et al. |
| 5,398,682 A | 3/1995 | Lynn |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,429,123 A | 7/1995 | Shaffer et al. |
| 5,437,272 A | 8/1995 | Fuhrman |
| 5,438,980 A | 8/1995 | Phillips |
| 5,443,075 A | 8/1995 | Holscher |
| 5,452,714 A | 9/1995 | Anderson et al. |
| 5,503,147 A | 4/1996 | Bertheau |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,535,738 A | 7/1996 | Estes et al. |
| 5,540,220 A | 7/1996 | Gropper et al. |
| 5,542,415 A | 8/1996 | Brady |
| 5,544,674 A | 8/1996 | Kelly |
| 5,549,106 A | 8/1996 | Gruenke et al. |
| 5,551,419 A | 9/1996 | Froehlich et al. |
| 5,596,984 A | 1/1997 | O'Mahony et al. |
| 5,605,151 A | 2/1997 | Lynn |
| 5,623,923 A | 4/1997 | Bertheau et al. |
| 5,630,411 A | 5/1997 | Holscher |
| 5,632,270 A | 5/1997 | O'Mahony et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,664,563 A | 9/1997 | Schroeder et al. |
| 5,671,767 A | 9/1997 | Kelly |
| 5,672,041 A | 9/1997 | Ringdahl et al. |
| 5,673,689 A | 10/1997 | Power |
| 5,692,497 A | 12/1997 | Schnitzer et al. |
| 5,694,926 A | 12/1997 | DeVries et al. |
| 5,715,812 A | 2/1998 | Deighan et al. |
| 5,752,509 A | 5/1998 | Lachmann et al. |
| 5,762,480 A | 6/1998 | Adahan |
| 5,771,884 A | 6/1998 | Yarnall et al. |
| 5,791,339 A | 8/1998 | Winter |
| 5,794,986 A | 8/1998 | Gansel et al. |
| 5,813,399 A | 9/1998 | Isaza et al. |
| 5,826,575 A | 10/1998 | Lall |
| 5,829,441 A | 11/1998 | Kidd et al. |
| 5,862,802 A | 1/1999 | Bird |
| 5,864,938 A | 2/1999 | Gansel et al. |
| 5,865,168 A | 2/1999 | Isaza |
| 5,868,133 A | 2/1999 | DeVries et al. |
| 5,881,717 A | 3/1999 | Isaza |
| 5,881,722 A | 3/1999 | DeVries et al. |
| 5,881,723 A | 3/1999 | Wallace et al. |
| 5,884,623 A | 3/1999 | Winter |
| 5,891,023 A | 4/1999 | Lynn |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,925,831 A | 7/1999 | Storsved |
| 5,931,160 A | 8/1999 | Gilmore et al. |
| 5,934,274 A | 8/1999 | Merrick et al. |
| 6,013,619 A | 1/2000 | Cochrane et al. |
| 6,024,089 A | 2/2000 | Wallace et al. |
| 6,041,780 A | 3/2000 | Richard et al. |
| 6,047,860 A | 4/2000 | Sanders |
| 6,076,523 A | 6/2000 | Jones et al. |
| 6,089,105 A | 7/2000 | Ricciardelli |
| 6,116,240 A | 9/2000 | Merrick et al. |
| 6,116,464 A | 9/2000 | Sanders |
| 6,123,073 A | 9/2000 | Schlawin et al. |
| 6,123,074 A | 9/2000 | Hete et al. |
| 6,135,106 A | 10/2000 | Dirks et al. |
| 6,142,150 A | 11/2000 | O'Mahoney |
| 6,148,814 A | 11/2000 | Clemmer et al. |
| 6,158,432 A | 12/2000 | Biondi et al. |
| 6,158,434 A | 12/2000 | Lugtigheid et al. |
| 6,161,539 A | 12/2000 | Winter |
| 6,220,245 B1 | 4/2001 | Takabayashi et al. |
| 6,223,064 B1 | 4/2001 | Lynn et al. |
| 6,269,812 B1 | 8/2001 | Wallace et al. |
| 6,273,444 B1 | 8/2001 | Power |
| 6,283,119 B1 | 9/2001 | Bourdon |
| 6,305,373 B1 | 10/2001 | Wallace et al. |
| 6,321,748 B1 | 11/2001 | O'Mahoney |
| 6,325,785 B1 | 12/2001 | Babkes et al. |
| 6,342,039 B1 | 1/2002 | Lynn et al. |
| 6,357,438 B1 | 3/2002 | Hansen |
| 6,358,215 B1 | 3/2002 | Ricciardelli |
| 6,360,745 B1 | 3/2002 | Wallace et al. |
| 6,369,838 B1 | 4/2002 | Wallace et al. |
| 6,371,114 B1 | 4/2002 | Schmidt et al. |
| 6,390,091 B1 | 5/2002 | Banner et al. |
| 6,412,483 B1 | 7/2002 | Jones et al. |
| 6,439,229 B1 | 8/2002 | Du et al. |
| 6,463,930 B2 | 10/2002 | Biondi et al. |
| 6,467,478 B1 | 10/2002 | Merrick et al. |
| 6,512,938 B2 | 1/2003 | Claure et al. |
| 6,526,970 B2 | 3/2003 | DeVries et al. |
| 6,532,958 B1 | 3/2003 | Buan et al. |
| 6,532,959 B1 | 3/2003 | Berthon-Jones |
| 6,532,960 B1 | 3/2003 | Yurko |
| 6,533,730 B2 | 3/2003 | Strom |
| 6,536,429 B1 | 3/2003 | Pavlov et al. |
| 6,543,449 B1 | 4/2003 | Woodring et al. |
| 6,546,930 B1 | 4/2003 | Emerson et al. |
| 6,553,991 B1 | 4/2003 | Isaza |
| 6,557,553 B1 | 5/2003 | Borrello |
| 6,561,187 B2 | 5/2003 | Schmidt et al. |
| 6,571,795 B2 | 6/2003 | Bourdon |
| 6,584,973 B1 | 7/2003 | Biondi et al. |
| 6,609,016 B1 | 8/2003 | Lynn |
| 6,622,726 B1 | 9/2003 | Du |
| 6,640,806 B2 | 11/2003 | Yurko |
| 6,644,310 B1 | 11/2003 | Delache et al. |
| 6,644,312 B2 | 11/2003 | Berthon-Jones et al. |
| 6,659,962 B2 | 12/2003 | Ricciardelli |
| 6,668,824 B1 | 12/2003 | Isaza et al. |
| 6,668,829 B2 | 12/2003 | Biondi et al. |
| 6,671,529 B2 | 12/2003 | Claure et al. |
| 6,675,801 B2 | 1/2004 | Wallace et al. |
| 6,688,307 B2 | 2/2004 | Berthon-Jones |
| 6,718,974 B1 | 4/2004 | Moberg |
| 6,718,975 B2 | 4/2004 | Blomberg |
| 6,723,055 B2 | 4/2004 | Hoffman |
| 6,725,447 B1 | 4/2004 | Gilman et al. |
| 6,739,337 B2 | 5/2004 | Isaza |

(56) References Cited

U.S. PATENT DOCUMENTS

| | | | |
|---|---|---|---|
| 6,745,764 B2 | 6/2004 | Hickle |
| 6,748,252 B2 | 6/2004 | Lynn et al. |
| 6,752,151 B2 | 6/2004 | Hill |
| 6,758,216 B1 | 7/2004 | Berthon-Jones et al. |
| 6,760,608 B2 | 7/2004 | Lynn |
| 6,761,165 B2 | 7/2004 | Strickland, Jr. |
| 6,761,167 B1 | 7/2004 | Nadjafizadeh et al. |
| 6,761,168 B1 | 7/2004 | Nadjafizadeh et al. |
| 6,796,305 B1 | 9/2004 | Banner et al. |
| 6,807,965 B1 | 10/2004 | Hickle |
| 6,814,074 B1 | 11/2004 | Nadjafizadeh et al. |
| 6,820,618 B2 | 11/2004 | Banner et al. |
| 6,830,048 B2 | 12/2004 | Wruck et al. |
| 6,837,242 B2 | 1/2005 | Younes |
| 6,839,753 B2 | 1/2005 | Biondi et al. |
| 6,866,040 B1 | 3/2005 | Bourdon |
| 6,868,346 B2 | 3/2005 | Larson et al. |
| 6,871,645 B2 | 3/2005 | Wartman et al. |
| 6,877,511 B2 | 4/2005 | DeVries et al. |
| 6,895,963 B1 | 5/2005 | Martin et al. |
| 6,938,619 B1 | 9/2005 | Hickle |
| 6,960,854 B2 | 11/2005 | Nadjafizadeh et al. |
| 6,986,347 B2 | 1/2006 | Hickle |
| 7,008,380 B1 | 3/2006 | Rees et al. |
| 7,017,574 B2 | 3/2006 | Biondi et al. |
| 7,036,504 B2 | 5/2006 | Wallace et al. |
| 7,066,173 B2 | 6/2006 | Banner et al. |
| 7,077,131 B2 | 7/2006 | Hansen |
| 7,081,095 B2 | 7/2006 | Lynn et al. |
| RE39,225 E | 8/2006 | Isaza et al. |
| 7,089,936 B2 | 8/2006 | Madaus et al. |
| 7,089,937 B2 | 8/2006 | Berthon-Jones et al. |
| 7,092,757 B2 | 8/2006 | Larson et al. |
| 7,100,609 B2 | 9/2006 | Berthon-Jones et al. |
| 7,117,438 B2 | 10/2006 | Wallace et al. |
| 7,152,598 B2 | 12/2006 | Morris et al. |
| 7,152,604 B2 | 12/2006 | Hickle et al. |
| 7,210,478 B2 | 5/2007 | Banner et al. |
| 7,222,623 B2 | 5/2007 | DeVries et al. |
| 7,229,430 B2 | 6/2007 | Hickle et al. |
| 7,267,122 B2 | 9/2007 | Hill |
| 7,270,126 B2 | 9/2007 | Wallace et al. |
| 7,275,540 B2 | 10/2007 | Bolam et al. |
| 7,296,573 B2 | 11/2007 | Estes et al. |
| 7,297,119 B2 | 11/2007 | Westbrook et al. |
| 7,308,894 B2 | 12/2007 | Hickle |
| 7,316,231 B2 | 1/2008 | Hickle |
| 7,331,343 B2 | 2/2008 | Schmidt et al. |
| 7,334,578 B2 | 2/2008 | Biondi et al. |
| 7,337,778 B2 | 3/2008 | Martin et al. |
| 7,353,824 B1 | 4/2008 | Forsyth et al. |
| 7,369,757 B2 | 5/2008 | Farbarik |
| 7,370,650 B2 | 5/2008 | Nadjafizadeh et al. |
| 7,398,115 B2 | 7/2008 | Lynn |
| 7,406,870 B2 | 8/2008 | Seto |
| 7,428,902 B2 | 9/2008 | Du et al. |
| 7,448,381 B2 | 11/2008 | Sasaki et al. |
| 7,455,583 B2 | 11/2008 | Taya |
| 7,460,959 B2 | 12/2008 | Jafari |
| 7,472,702 B2 | 1/2009 | Beck et al. |
| 7,487,773 B2 | 2/2009 | Li |
| 7,509,957 B2 | 3/2009 | Duquette et al. |
| 7,520,279 B2 | 4/2009 | Berthon-Jones |
| 7,527,054 B2 | 5/2009 | Misholi |
| 7,565,905 B2 | 7/2009 | Hickle |
| 7,654,802 B2 | 2/2010 | Crawford, Jr. et al. |
| 7,668,579 B2 | 2/2010 | Lynn |
| 7,694,677 B2 | 4/2010 | Tang |
| 7,717,113 B2 | 5/2010 | Andrieux |
| D618,356 S | 6/2010 | Ross |
| 7,758,503 B2 | 7/2010 | Lynn et al. |
| 7,784,461 B2 | 8/2010 | Figueiredo et al. |
| 7,802,571 B2 | 9/2010 | Tehrani |
| 7,814,906 B2 | 10/2010 | Moretti |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2002/0185126 A1 | 12/2002 | Krebs |
| 2003/0209242 A1 | 11/2003 | Hickle |
| 2003/0217747 A1 | 11/2003 | Hickle et al. |
| 2005/0039748 A1 | 2/2005 | Andrieux |
| 2005/0070477 A1 | 3/2005 | Cochrane |
| 2005/0112325 A1 | 5/2005 | Hickle |
| 2005/0139212 A1 | 6/2005 | Bourdon |
| 2005/0150494 A1 | 7/2005 | DeVries et al. |
| 2005/0172965 A1 | 8/2005 | Thulin |
| 2005/0188083 A1 | 8/2005 | Biondi et al. |
| 2005/0247311 A1 | 11/2005 | Vacchiano et al. |
| 2006/0112959 A1 | 6/2006 | Mechlenburg et al. |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0189880 A1 | 8/2006 | Lynn et al. |
| 2006/0195041 A1 | 8/2006 | Lynn et al. |
| 2006/0235324 A1 | 10/2006 | Lynn |
| 2006/0241708 A1 | 10/2006 | Boute |
| 2006/0264762 A1 | 11/2006 | Starr |
| 2006/0266355 A1* | 11/2006 | Misholi .............. 128/204.23 |
| 2006/0272642 A1 | 12/2006 | Chalvignac |
| 2006/0286038 A1 | 12/2006 | Rairkar et al. |
| 2007/0000494 A1 | 1/2007 | Banner et al. |
| 2007/0017515 A1 | 1/2007 | Wallace et al. |
| 2007/0027375 A1 | 2/2007 | Melker et al. |
| 2007/0028921 A1 | 2/2007 | Banner et al. |
| 2007/0044805 A1 | 3/2007 | Wedler et al. |
| 2007/0072541 A1 | 3/2007 | Daniels II, et al. |
| 2007/0077200 A1 | 4/2007 | Baker |
| 2007/0093721 A1 | 4/2007 | Lynn et al. |
| 2007/0095347 A1 | 5/2007 | Lampotang et al. |
| 2007/0107728 A1 | 5/2007 | Ricciardelli et al. |
| 2007/0129647 A1 | 6/2007 | Lynn |
| 2007/0142716 A1 | 6/2007 | Biondi |
| 2007/0144521 A1 | 6/2007 | DeVries et al. |
| 2007/0149860 A1 | 6/2007 | Lynn et al. |
| 2007/0157931 A1 | 7/2007 | Parker et al. |
| 2007/0163579 A1 | 7/2007 | Li et al. |
| 2007/0191697 A1 | 8/2007 | Lynn et al. |
| 2007/0215154 A1 | 9/2007 | Borrello |
| 2007/0227537 A1 | 10/2007 | Bemister et al. |
| 2007/0272241 A1 | 11/2007 | Sanborn et al. |
| 2007/0277823 A1 | 12/2007 | Al-Ali et al. |
| 2007/0284361 A1 | 12/2007 | Nadjafizadeh et al. |
| 2008/0000479 A1 | 1/2008 | Elaz et al. |
| 2008/0053441 A1 | 3/2008 | Gottlib et al. |
| 2008/0066752 A1 | 3/2008 | Baker et al. |
| 2008/0066753 A1 | 3/2008 | Martin et al. |
| 2008/0072896 A1 | 3/2008 | Setzer et al. |

(56) References Cited

U.S. PATENT DOCUMENTS

| | | |
|---|---|---|
| 2008/0072902 A1 | 3/2008 | Setzer et al. |
| 2008/0078390 A1 | 4/2008 | Milne et al. |
| 2008/0081974 A1 | 4/2008 | Pav |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0110461 A1 | 5/2008 | Mulqueeny et al. |
| 2008/0119753 A1 | 5/2008 | Ricciardelli et al. |
| 2008/0178880 A1 | 7/2008 | Christopher et al. |
| 2008/0178882 A1 | 7/2008 | Christopher et al. |
| 2008/0200775 A1 | 8/2008 | Lynn |
| 2008/0200819 A1 | 8/2008 | Lynn et al. |
| 2008/0236582 A1 | 10/2008 | Tehrani |
| 2008/0251079 A1 | 10/2008 | Richey |
| 2008/0314385 A1 | 12/2008 | Brunner et al. |
| 2009/0165795 A1 | 7/2009 | Nadjafizadeh et al. |
| 2009/0171176 A1 | 7/2009 | Andersohn |
| 2009/0171226 A1 | 7/2009 | Campbell et al. |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0006098 A1 | 1/2010 | McGinnis et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0186742 A1 | 7/2010 | Sherman et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0282259 A1 | 11/2010 | Figueiredo et al. |
| 2010/0288283 A1 | 11/2010 | Campbell et al. |
| 2010/0292544 A1 | 11/2010 | Sherman et al. |
| 2010/0300446 A1 | 12/2010 | Nicolazzi et al. |
| 2010/0331639 A1 | 12/2010 | O'Reilly |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0304995 A1 | 12/2012 | Kauc |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0025596 A1 | 1/2013 | Jafari et al. |
| 2013/0025597 A1 | 1/2013 | Doyle et al. |
| 2013/0053717 A1* | 2/2013 | Vandine et al. ............... 600/532 |

FOREIGN PATENT DOCUMENTS

| | | |
|---|---|---|
| WO | WO2007085110 | 8/2007 |
| WO | WO2007145948 | 12/2007 |

OTHER PUBLICATIONS

7200 Ventilatory System: Addendum/Errata. Nellcor Puritan Bennett, Part No. 4-023576-00, Rev. A, Apr. 1988, pp. 1-32.

800 Operator's and Technical Reference Manual. Series Ventilator System, Nellcor Puritan Bennett, Part No. 4-070088-00, Rev. L, Aug. 2010, pp. 1-476.

(56) References Cited

OTHER PUBLICATIONS

840 Operator's and Technical Reference Manual. Ventilator System, Nellcor Puritan Bennett, Part No. 4-075609-00, Rev. G, Oct. 2006, pp. 1-424.

Claure, Nelson, MSc., PhD. et al., Graph from "Automated Adjustment of Inspired Oxygen in Preterm Infants with Frequent Fluctuations in Oxygenation: A Pilot Clinical Trial", The Journal of Pediatrics, 2009; 155: pp. 640-645 (1 page).

\* cited by examiner

METHODS AND SYSTEMS FOR GATING USER INITIATED INCREASES IN OXYGEN CONCENTRATION DURING VENTILATION

INTRODUCTION

Medical ventilator systems have long been used to provide ventilatory and supplemental oxygen support to patients. These ventilators typically comprise a source of pressurized oxygen which is fluidly connected to the patient through a conduit or tubing. As each patient may require a different ventilation strategy, modern ventilators can be customized for the particular needs of an individual patient. For example, preterm infants are subject to frequent episodes of spontaneous hypoxia. Accordingly, some ventilators offer a function that allows the user to increase the oxygen concentration by a fixed amount for a fixed period (i.e. a 20% increase in fractional inspired oxygen ($FiO_2$) for two minutes).

Gating User Initiated Increases in Oxygen Concentration During Ventilation

This disclosure describes systems and methods for ventilating a patient. The disclosure describes novel systems and methods for preventing and/or reducing the likelihood of a patient from receiving too much oxygen during a selected limited increase in oxygen concentration for a set period of time.

One aspect of the disclosure relates to a method for operating a ventilator. The method includes:

a) delivering a regular oxygen concentration to a patient during ventilation;

b) receiving a user selection of a limited oxygen concentration increase for a set time period;

c) delivering a selected oxygen concentration above the regular oxygen concentration based on the received user selection;

d) monitoring an oxygen saturation level of blood in the patient during the step of delivering the selected oxygen concentration;

e) determining that the oxygen saturation level of the blood exceeds a predetermined threshold prior to expiration of the set time period for the limited oxygen concentration increase; and f) delivering an adjusted oxygen concentration to the patient based on the step of determining.

Another aspect of the disclosure relates to a ventilator system that includes a user interface, an Oxygen Increase Option, at least one processor and at least one memory. The Oxygen Increase Option is selectable via the user interface. The Oxygen Increase Option instructs a ventilator system to deliver a selected oxygen concentration above a regular oxygen concentration during ventilation of a patient for a set time period. The memory is communicatively coupled to the at least one processor and contains instructions for operating the ventilator system after receiving a user selection of the Oxygen Increase Option that, when executed by the at least one processor, performs a method. The method includes:

a) monitoring an oxygen saturation level of blood in the patient;

b) determining that the oxygen saturation level of the blood exceeds a predetermined threshold prior to expiration of the set time period; and c) delivering an adjusted oxygen concentration to the patient based on the step of determining.

An additional aspect of this disclosure relates to a computer-readable medium having computer-executable instructions for performing a method of ventilating a patient with a ventilator. The method includes:

a) repeatedly delivering a regular oxygen concentration to a patient during ventilation;

b) repeatedly receiving a user selection of a limited oxygen concentration increase for a set time period;

c) repeatedly delivering a selected oxygen concentration above the regular oxygen concentration based on the received user selection;

d) repeatedly monitoring an oxygen saturation level of blood in the patient during the step of delivering the selected oxygen concentration;

e) repeatedly determining that the oxygen saturation level of the blood exceeds a predetermined threshold prior to expiration of the set time period for the limited oxygen concentration increase; and f) repeatedly delivering an adjusted oxygen concentration to the patient based on the step of determining.

Yet another aspect of the disclosure relates to ventilator system. The ventilator system includes means for delivering a regular oxygen concentration to a patient during ventilation; means for receiving a user selection of a limited oxygen concentration increase for a set time period; means for delivering a selected oxygen concentration above the regular oxygen concentration based on the received user selection; means for monitoring an oxygen saturation level of blood in the patient during the step of delivering the selected oxygen concentration; means for determining that the oxygen saturation level of the blood exceeds a predetermined threshold prior to expiration of the set time period for the limited oxygen concentration increase; and means for delivering an adjusted oxygen concentration to the patient based on the step of determining.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiments of systems and methods described below and are not meant to limit the scope of the invention in any manner.

DETAILED DESCRIPTION

Figure 1:
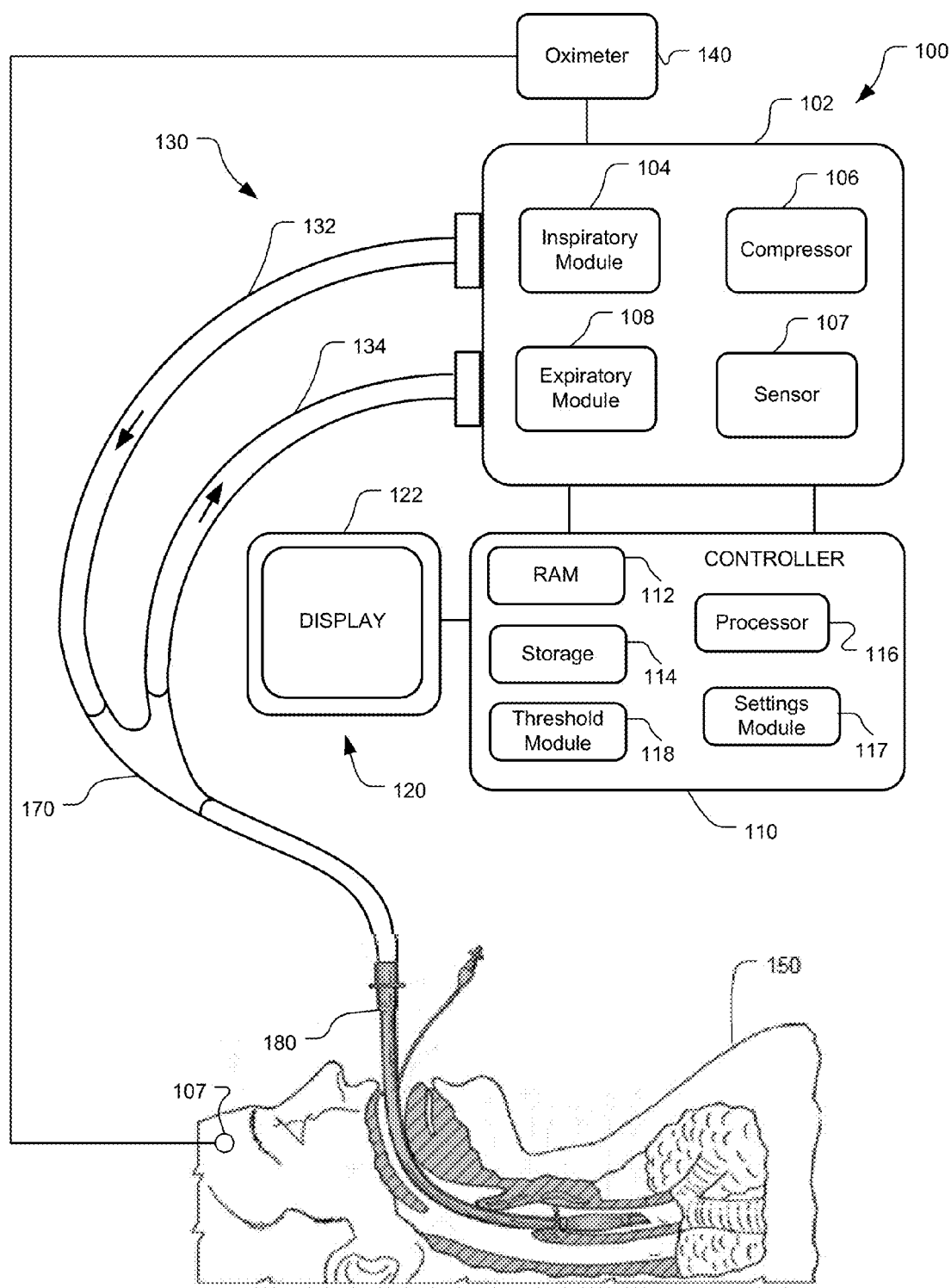
FIG. 1 illustrates an embodiment of a ventilator.

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

While operating a ventilator, it is desirable to control the percentage of oxygen in the gas supplied by the ventilator to the patient. Further, it is desirable to monitor oxygen saturation level of the blood ($SpO_2$ level) of a patient. Accordingly, medical ventilator systems may be combined with and/or include a system for monitoring the blood oxygen level of a patient, such as an oximeter.

Additionally, as each patient may require a different ventilation strategy, modern ventilators can be customized for the particular needs of an individual patient. For example, ventilation of preterm infants typically requires oxygen concentrations of greater than 21%. Further, preterm infants are subject to frequent episodes of spontaneous hypoxia. Accordingly, some ventilators offer a function that allows the user to increase the oxygen concentration by a fixed amount for a set time period (e.g. a 20% increase in fractional inspired oxygen ($FiO_2$) for two minutes) referred to herein as an "Oxygen Increase Option". Originally the Oxygen Increase Option was designed to deliver increased oxygen during suctioning of the patient airway. Clinicians, knowing the functionality of the Oxygen Increase Option, began to utilize the Oxygen Increase Option to address the frequent episodes of spontaneous hypoxia of preterm infants. Accordingly, now the use of the Oxygen Increase Option is regularly utilized by clinicians to address the frequent episodes of spontaneous hypoxia of preterm infants.

However, because of the immature development of the lungs and retina, elevated oxygen levels also place preterm infants at greater risk for lung and retinal injury. Many times these predetermined increases in oxygen concentrations for the predetermined amount of time are more than is necessary in order to address a transient occurrence of hypoxemia. Accordingly, the use of the Oxygen Increase Option exposes patients, such as preterm infants, to high levels of oxygen for longer than needed, which places patients at risk for lung, retinal, and other injuries associated with exposure to elevated levels of oxygen.

Accordingly, there is a need for providing increased oxygen for a period of time while preventing a patient from receiving too much oxygen for longer than needed to prevent injury to the patient. The present disclosure describes novel methods and systems for ventilating a patient that monitors the $SpO_2$ level of a patient during an Oxygen Increase Option and automatically reduces the increased oxygen level if the $SpO_2$ level of the patient exceeds a predetermined threshold. In some embodiments, the ventilator additionally automatically reduces the set time period of the Oxygen Increase Option if the $SpO_2$ level of the patient exceeds a predetermined threshold.

FIG. 1 is a diagram illustrating an embodiment of an exemplary ventilator 100 connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180. The pneumatic system 102 generates a flow of breathing gas through the ventilation tubing system 130.

Ventilation tubing system 130 (or patient circuit 130) may be a two-limb (shown) or a one-limb circuit for carrying gases to and from the patient 150. In a two-limb embodiment, a fitting, typically referred to as a "wye-fitting" 170, may be provided to couple a patient interface 180 (as shown, an endotracheal tube) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 and the expiratory module 108 to provide a gas source for ventilatory support via inspiratory limb 132.

The inspiratory module 104 is configured to deliver gases to the patient 150 according to prescribed ventilatory settings. In some embodiments, inspiratory module 104 is configured to provide ventilation according to a breath type or a selected option, The expiratory module 108 is configured to release gases from the patient's lungs according to prescribed ventilatory settings. Specifically, expiratory module 108 is associated with and/or controls an expiratory valve for releasing gases from the patient 150.

The ventilator 100 may also include one or more sensors 107 communicatively coupled to ventilator 100. The sensors 107 may be located in the pneumatic system 102, ventilation tubing system 130, and/or on the patient 150. The embodiment of FIG. 1 illustrates a sensor 107 in pneumatic system 102 and a sensor 107 on the patient 150.

Sensors 107 may communicate with various components of ventilator 100, e.g., pneumatic system 102, other sensors 107, processor 116, oximeter 140, settings module 117, threshold module 118, and/or any other suitable components and/or modules. In one embodiment, sensors 107 generate output and send this output to pneumatic system 102, other sensors 107, processor 116, settings module 117, threshold module 118, oximeter 140, and/or any other suitable components and/or modules. Sensors 107 may employ any suitable sensory or derivative technique for monitoring one or more patient parameters or ventilator parameters associated with the ventilation of a patient 150. Sensors 107 may detect changes in patient parameters indicative of patient triggering, for example. Sensors 107 may be placed in any suitable location, within the ventilatory circuitry or other devices communicatively coupled to the ventilator 100. Further, sensors 107 may be placed in any suitable internal location, such as, within the ventilatory circuitry or within components or modules of ventilator 100. For example, sensors 107 may be coupled to the inspiratory and/or expiratory modules for detecting changes in, for example, circuit pressure and/or flow. In other examples, sensors 107 may be affixed to the ventilatory tubing or may be embedded in the tubing itself. According to some embodiments, sensors 107 may be provided at or near the lungs (or diaphragm) for detecting a pressure in the lungs or on the patient 150 for detecting $SpO_2$.

Additionally or alternatively, sensors 107 may be affixed or embedded in or near wye-fitting 170 and/or patient interface 180. Indeed, any sensory device useful for monitoring changes in measurable parameters during ventilatory treatment may be employed in accordance with embodiments described herein.

As should be appreciated, with reference to the Equation of Motion for the lung, ventilatory parameters are highly interrelated and, according to embodiments, may be either directly or indirectly monitored. That is, parameters may be directly monitored by one or more sensors 107, as described above, or may be indirectly monitored or estimated by derivation, such as the Equation of Motion for the lung.

The ventilator 100 may also include a system or module for monitoring the $SpO_2$ of the patient 150. In one embodiment, as illustrated in FIG. 1, the ventilator 100 includes an oximeter 140 for monitoring the $SpO_2$ of the patient 150. In this embodiment, the oximeter 140 is connected to a patient 150 via sensor 107. As illustrated, in some embodiments, the oximeter 140 is a completely separate and independent component from the ventilator 100. In alternative embodiments, the oximeter 140 is part of the ventilator 100 and/or the pneumatic system 102.

The oximeter 140 determines an oxygen gas saturation level of blood in the patient 150 based on the patient readings taken by a sensor 107 during ventilation of patient 150 by the ventilator 100. The oximeter 140 sends the measured oxygen saturation level of the blood of patient 150 to a controller 110, processor 116, threshold module 118, settings module 117, and/or any other suitable component of the ventilator 100.

The pneumatic system 102 may include a variety of other components, including mixing modules, valves, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.).

In one embodiment, the operator interface 120 of the ventilator 100 includes a display 122 communicatively coupled to ventilator 100. Display 122 provides various input screens, for receiving clinician input, and various display screens, for presenting useful information to the clinician. In one embodiment, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122. For example, the operator may select or input an Oxygen Increase Option via the operator interface 120.

Display 122 may also provide useful information in the form of various ventilatory data regarding the physical condition of a patient 150. The useful information may be derived by the ventilator 100, based on data collected by a processor 116, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system coupled via any suitable means to the ventilator 100. For example, the display 122 may display the oxygen percentage increase and/or the set time period for the Oxygen Increase Option and/or the activation of an Oxygen Increase Option. In other embodiments, the display 122 may display the $SpO_2$ concentration of the patient 150 during delivery of an Oxygen Increase Option, the early termination of an Oxygen Increase Option, the reduction of a set time period for an Oxygen Increase Option, the reduction of an oxygen increase for an Oxygen Increase Option, and/or a predetermined $SpO_2$ threshold for the threshold module 118.

The Oxygen Increase Option is a button or option provided to the operator that increases the concentration of oxygen delivered to the patient 150 for a set time period. The increase in oxygen concentration and/or the set time period may be selected or input by the operator, may be predetermined based on the ventilator configuration, and/or may be determined by the ventilator 100 based on patient settings and/or ventilator settings. The increased concentration in oxygen from Oxygen Increase Option is also referred to herein as the "selected oxygen concentration." For example, the Oxygen Increase Option may increase the $FiO_2$ delivered to the patient 150 by about 20% for about two minutes. In other examples, the Oxygen Increase Option may increase the $FiO_2$ delivered to the patient 150 by 15% for one minute. These examples are not meant to be limiting. The Oxygen Increase Option may utilize any suitable increase in oxygen concentration for any suitable time period as would be known by a person of skill in the art.

Controller 110 may include memory 112, one or more processors 116, storage 114, and/or other components of the type commonly found in command and control computing devices. Controller 110 may further include a settings module 117 and/or a threshold module 118 configured to deliver gases to the patient 150 according to prescribed breath types or user selected option, as illustrated in FIG. 1. In alternative embodiments, the settings module 117 and/or the threshold module 118 may be located in other components of the ventilator 100, such as the pressure generating system 102 (also known as the pneumatic system 102).

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

As illustrated, the ventilator 100 includes a settings module 117. The inspiratory module 104 receives instructions from the settings module 117 for delivering a breath to the patient 150. The settings module 117 may send instructions based on ventilator settings and/or patient parameters. Ventilator settings include any setting selected and or determined by the ventilator 100 and/or input by the operator, such as breath type, ventilation mode, respiration rate, tidal volume and etc. Patient parameters include any measured, monitored, derived, and input patient parameter, such as ideal body weight, height, age, sex, work of breathing, $SpO_2$, heart rate, age, respiration rate, etc. Accordingly, the settings module 117 will change the instructions provided to the inspiratory module 104 based on operator selections and/or inputs. Further, in some embodiments, the expiratory module 108 receives instructions from the settings module 117 for releasing gases from the patient's lungs. For example, if the setting module receives an operator selection or input of an Oxygen Increase Option via the operator interface 120, the settings module 117 will send instructions to the inspiratory module 104 to increase the concentration of oxygen by a predetermined amount for a set time period. As discussed above, the concentration of oxygen delivered during the Oxygen Increase Option is also referred to herein as the selected oxygen concentration.

In some embodiments, the ventilator 100 also includes a threshold module 118 as illustrated in FIG. 1. The threshold module 118 monitors the $SpO_2$ of the patient 150 during an Oxygen Increase Option. The threshold module 118 receives $SpO_2$ measurements of the patient 150 from the system or module for monitoring the $SpO_2$ of the patient 150, such as the oximeter 140. The threshold module 118 compares the patient's $SpO_2$ levels or measurements to a predetermined threshold for the set time period associated with the Oxygen Increase Option. The predetermined threshold may be input or selected by an operator, set during the configuration of the ventilator 100, or determined/derived by the ventilator 100 based on patient parameters and/or ventilator settings. In some embodiments, the predetermined threshold is a $SpO_2$ of 95%. In other embodiments, the predetermined threshold is a $SpO_2$ of 90%. In some embodiments, the predetermined threshold is a percent increase in $SpO_2$, such as a 25% increase in $SpO_2$ within 45 seconds. In other embodiments, the predetermined threshold is a 25% increase in slope of $SpO_2$. The embodiments listed are not limiting. Any suitable predetermined threshold for preventing a patient 150 from receiving too much oxygen may be utilized as would be known by a person of skill in the art, Further, in some embodiments, the predetermined threshold may be adjusted or based at least in part on patient parameters and/or ventilator settings.

As discussed above, the threshold module 118 only compares the $SpO_2$ of the patient to the predetermined threshold during the set time period of the Operator Increase Option. Accordingly, if the threshold module determines that the set time period for the Oxygen Increase Option expires, the threshold module 118 notifies the settings module 117 of the time period expiration. The settings module 117 based on the received notice of the time period expiration from the threshold module 118, sends instructions to the inspiratory module 104 to reduce the oxygen concentration to the regular (or normal) oxygen concentration, which effectively ends the Oxygen Increase Option.

If the threshold module 118 determines that the patient's $SpO_2$ is below the predetermined threshold, the threshold module 118 continues to the compares the next newly received $SpO_2$ measurement of the patient 150 to the predetermined threshold until the set time period for the Oxygen Increase Option expires or a patient's $SpO_2$ levels exceed the predetermined threshold. If the threshold module 118 determines that the patient's $SpO_2$ is above or exceeds the predetermined threshold, the threshold module 118 determines that the patient 150 is receiving too high a concentration of oxygen and communicates this determination to settings module 117.

The settings module 117, based on the receipt of the threshold violation from the threshold module 118, sends instructions to the inspiratory module 104 to reduce the concentration of oxygen delivered to patient 150. The reduced oxygen concentration delivered to the patient based on the receipt of a threshold violation is also referred to herein as the adjusted oxygen concentration. The adjusted oxygen concentration is an oxygen concentration that is less than the selected oxygen concentration delivered to the patient during an Oxygen Increase Option and is equal or greater than the regular oxygen concentration delivered to the patient prior to the selection of the Oxygen Increase Option. For example, in some embodiments, the settings module 117 reduces the oxygen concentration delivered to the patient 150 to the regular oxygen concentration or the amount delivered to the patient 150 prior to the operator selection or input of the Oxygen Increase Option and effectively ends the Oxygen Increase Option. In other embodiments, the settings module 117 reduces the selected oxygen concentration delivered to the patient 150 by a set percentages or amount, such as by at least 5%, 10%, 30%, or 50% until the set time period of the Oxygen Increase Option expires. Once the setting module 117 receives notice of the time period expiration, the settings module 117 sends instruction to the inspiration module 104 to change the adjusted oxygen concentration to the regular oxygen concentration ending the Oxygen Increase Option. Accordingly, in these embodiments, the ventilator continues the Oxygen Increase Option by delivering the adjusted oxygen concentration until the set time period expires. In further embodiments, the settings module 117 in addition to decreasing the oxygen concentration delivered to the patient 150 also decreases the set time period for the Oxygen Increase Option. For example, the settings module 117 may reduce the set time period by at least 50%, 30%, 20%, 10% or 5%. As known by a person of skill in the art any suitable reduction of the set time period for preventing a patient 150 from receiving too much oxygen during an Oxygen Increase Option may be utilized. Thus, in these embodiments, the ventilator continues the Oxygen Increase Option by delivering the adjusted oxygen concentration until the reduced time period expires.

In some embodiments, the settings module 117 send instructions to the inspiratory module 104 to reduce the oxygen concentration to the new lower level immediately after receiving the threshold violation from the threshold module 118. For example, if the Oxygen Increase Option increased the oxygen percentage by 20%, the settings module 117 will send instructions to the inspiratory module 104 to decrease the amount of oxygen delivered to the patient 150 to the adjusted oxygen concentration immediately after receiving the threshold violation from the threshold module 118. In other embodiments, the settings module 117 sends instruction to the inspiratory module 104 to reduce the oxygen concentration to the new lower level gradually after receiving the threshold violation from the threshold module 118. For example, if the Oxygen Increase Option increased the oxygen percentage by 20%, the settings module 117 will send instructions to the inspiratory module 104 to decrease the amount of oxygen delivered to the patient 150 in increments of 5% every 10 seconds until the amount of oxygen delivered to the patient 150 reaches the adjusted oxygen concentration after receiving the threshold violation from the threshold module 118. Any suitable method or system as known by a person of a skill the art may be utilized to reduce the selected oxygen concentration and/or to reach the adjusted oxygen concentration.

Many times the selected oxygen concentration for the predetermined amount of time from the Oxygen Increase Option is more than is necessary in order to address a transient occurrence of hypoxemia or low oxygen levels in patients. The early termination or reduction of the increase oxygen delivery based on the monitoring of the patient's $SpO_2$ levels provided by ventilator 100 prevents and/or reduces the likelihood of patients, such as infants and preterm infants, from being exposed to high levels of oxygen for longer than needed, which places patients at risk for lung, retinal, and other injuries associated with exposure to elevated levels of oxygen. Accordingly, the ventilator 100 prevents and/or reduces the likelihood that a patient 150 will suffer from lung, retinal, and other injuries associated with exposure to elevated levels of oxygen.

Figure 2:
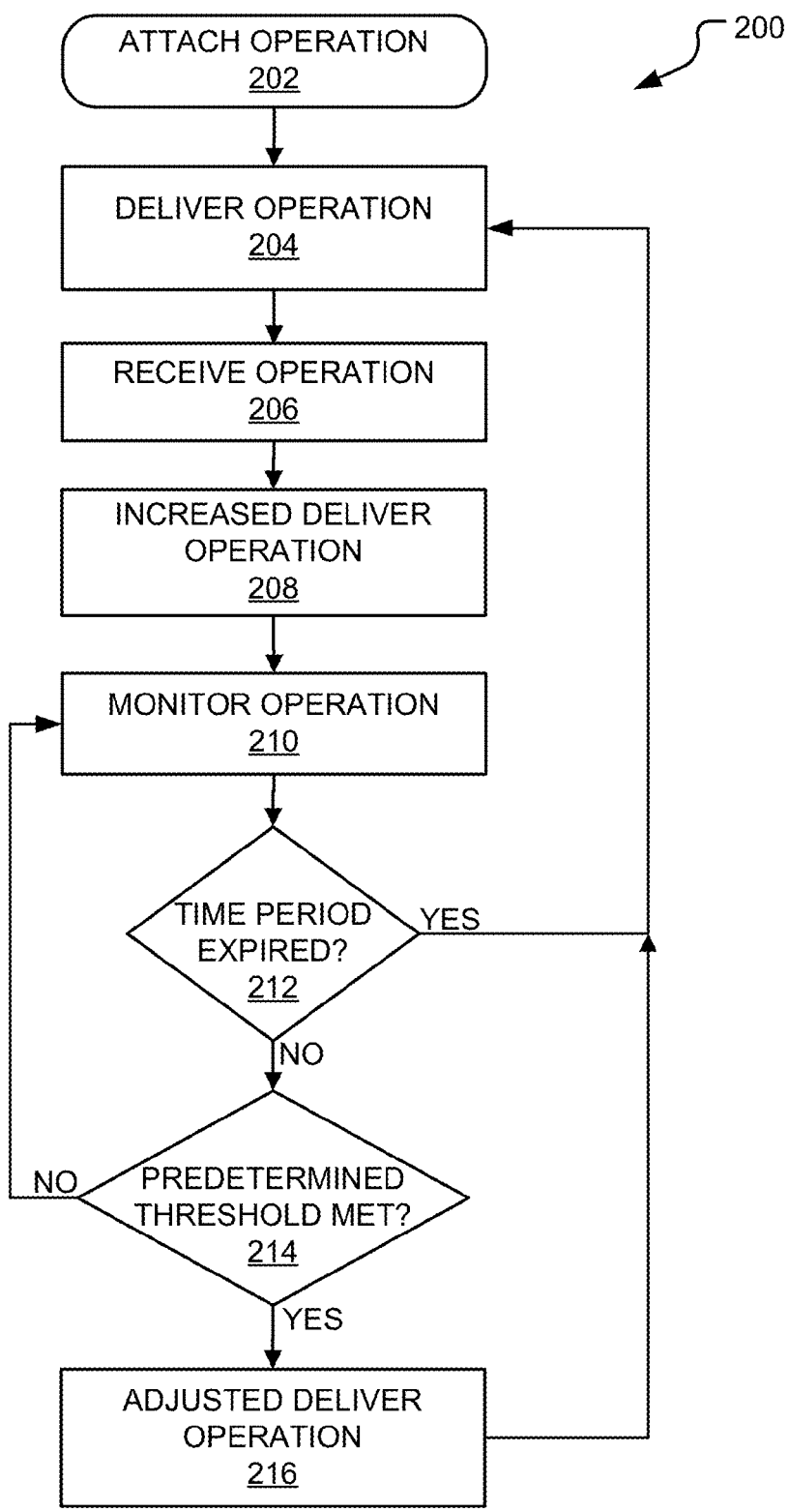
FIG. 2 illustrates an embodiment of a method for ventilating a patient on a ventilator.

FIG. 2 illustrates an embodiment of a method 200 for ventilating a patient. The method 200 for ventilating a patient reduces the likelihood of and/or prevents patients from receiving too much oxygen for longer than needed during the delivery of an Oxygen Increase Option. Accordingly, method 200 reduces and/or prevents patients, such as infants and preterm infants, from getting lung, retinal, and other injuries associated with exposure to elevated levels of oxygen. As illustrated, method 200 includes an attach operation 202. At attach operation 202, a patient is attached to a ventilator.

Further, method 200 includes a delivering or normal ventilation operation 204. During the delivering operation 204, the ventilator delivers a regular oxygen concentration to a patient during ventilation. The regular oxygen concentration is based on the normal ongoing ventilation of the patient. In some embodiments, the regular oxygen concentration and other ventilator settings delivered to the patient may be input or selected by the operator or determined by the ventilator based on ventilator settings and/or patient parameters. For example, in some embodiments, the regular oxygen concentration delivered to the patient may be based on the breath type delivered to the patient. In some embodiments, the regular oxygen concentration delivered to the patient is a $FiO_2$ from 10% to 40%.

Also, method 200 includes a receiving operation 206. During the receiving operation 206, the ventilator receives a user selection of a limited oxygen concentration increase for a set time period. For example, the ventilator receives the user selection of a limited oxygen concentration increase for a set time period when an operator selects or inputs an Oxygen Increase Option. The operator may input or select a limited oxygen concentration along with a set time period for the selected oxygen concentration via a user interface, a graphical user interface, a wheel, keyboard, mouse, and/or other suitable interactive device for receiving interface and input command operations. In some embodiments, the operator inputs or selects the amount of oxygen increase and/or the set time period. In alternative embodiments, the amount of oxygen increase and/or the set time period is preconfigured into the ventilator and/or determined by ventilator based on ventilator settings and/or patient parameters and only initiated after operator selection.

Method 200 includes an increased delivering operation 208. In response to the receiving operation 206, an increased delivering operation 208 is performed by the ventilator. During the increased delivering operation 208, the ventilator delivers a selected oxygen concentration above the regular oxygen concentration based on previously received user selections. In some embodiments, the limited oxygen increase is an about 20% increase in oxygen concentration for a set time period of about two minutes. For example, the ventilator may increase the $FiO_2$ delivered to the patient from 30% to 50% for two minutes. This example is not meant to be limiting. The ventilator may increase the delivered oxygen concentration by any suitable amount (e.g., 5%, 10%, 15%, 25%, 30%, 35%, etc.) for any suitable set time period (e.g., 45 seconds, 1 minute 1.5 minutes, 2.5 minutes, etc.) as would be known by a person of skill in the art. In some embodiments, the settings module 117, processor 116, and/or controller 110 send instructions to the pneumatic system 102 and/or inspiratory module 104 for the delivery of the selected oxygen concentration for the set time period.

As illustrated, method 200 includes a monitoring operation 210. During the increased delivering operation 208, the monitoring operation is performed by the ventilator. As part of the monitoring operation 210, the ventilator monitors an oxygen saturation level of blood in the patient during the delivery of the selected oxygen concentration. The monitoring operation 210 uses various sensors to monitor one or more parameters of the patient, e.g., $SpO_2$. The sensors may include any suitable sensing device as known by a person of skill in the art for monitoring the $SpO_2$ of a patient. In some embodiments, the sensors are part of a ventilator and/or an oximeter. In some embodiments, the ventilator during monitoring operation 210 monitors the $SpO_2$ levels of the patient periodically or continuously during the set time period of the delivery of the increase oxygen concentration. For example, the ventilator during the monitoring operation 210 may monitor the $SpO_2$ every computational cycle (e.g., 2 milliseconds, 5 milliseconds, 10 milliseconds, etc.). In other embodiments, the ventilator during the monitoring operation 210 may monitor $SpO_2$ after a predetermined amount of time or a predetermined event, such as set number of breaths.

In some embodiments, method 200 includes a time determination operation 212. During the time determination operation 212, the ventilator determines if the set time period for the limited oxygen concentration increase has expired. If the time period has expired, then the limited oxygen concentration increase has ended causing the ventilator to deliver the amount of oxygen delivered prior to the step of receiving a user selection of the limited oxygen concentration increase or the regular oxygen concentration. If the ventilator during the time determination operation 212 determines that the set time period for the limited oxygen concentration has expired, the ventilator selects to perform delivering operation 204. If the ventilator during the time determination operation 212 determines that the set time period for the limited oxygen concentration has not expired, the ventilator selects to perform threshold determination operation 214.

Method 200 includes a threshold determination operation 214. During the threshold determination operation 214, the ventilator determines if the oxygen saturation level of the blood of the patient exceeds a predetermined threshold. If the ventilator during the threshold determination operation 214 determines that the oxygen saturation level of the blood of the patient exceeds a predetermined threshold, the ventilator selects to perform adjusted delivering operation 216. If the ventilator during the threshold determination operation 214 determines that the oxygen saturation level of the blood of the patient does not exceed a predetermined threshold, the ventilator selects to perform monitoring operation 210.

The predetermined threshold may be input or selected by an operator, set during ventilator configuration, and/or determined by the ventilator based on ventilator settings and/or patient parameters, In some embodiments, the predetermined threshold is a $SpO_2$ level, a percent increase in $SpO_2$, a percent increase in $SpO_2$ in a certain amount of time, or a set increase in slope of $SpO_2$. This list is not meant to be limiting.

Any predetermined threshold for preventing a patient from receiving too much oxygen for an extended period of time as know by a person of skill in the art may be utilized, For example, the predetermined threshold may be a $SpO_2$ percentage of 90% or 95%. In another example, the predetermined threshold is a 20% increase in $SpO_2$ in a 20 second time frame. In some embodiments, the predetermined threshold may be based on a patient parameter, such as disease state, body surface area, height, weight, age, ideal or predicted body weight, and/or gender.

The monitor operation 210, the time determination operation 212, and the threshold determination operation 214 are all performed by the ventilator during the increased delivering operation 208. Further, the monitor operation 210, the time determination operation 212, and/or the threshold determination operation 214 may be performed by the ventilator continuously, periodically, after a set time period, every computational cycle (e.g., 2 milliseconds, 5 milliseconds, 10 milliseconds, etc.), or based on a predetermined event, such as set number of breaths during the increase delivering operation 208.

Further, method 200 includes an adjusted delivering operation 216. During the adjusted delivering operation 216, the ventilator delivers an adjusted oxygen concentration to the patient. The adjusted oxygen concentration is an oxygen concentration that is less than the selected oxygen concentration and equal to or greater than the regular oxygen concentration delivered before the ventilator received the user selection of a limited oxygen concentration increase for a set time period. For example, in some embodiments, if the ventilator determines that the $SpO_2$ level of the patient is above the predetermined threshold, the ventilator during the adjusted delivering operation 216 delivers the regular oxygen concentration or the oxygen concentration delivered to the patient prior to the increased delivering operation 208. In these embodiments, the ventilator during the adjusted delivery option 208 ends the increased delivery operation 208. In an alternative example, if the ventilator determines that the $SpO_2$ level of the patient exceeds the predetermined threshold, the ventilator during the adjusted delivering operation 216 decreases the selected oxygen concentration by a set percentage, such as 5%, 10%, 15%, 25%, 50%, 75%, 85%, etc. In other embodiments, the adjusted oxygen concentration reduces the selected oxygen concentration by at least 5%, by at least 10%, by at least 30%, and/or by at least 50%.

In some embodiments, the amount the selected oxygen concentration is reduced may be based on a patient parameter, such as disease state, body surface area, height, weight, age, ideal or predicted body weight, and/or gender. In other embodiments, the ventilator during the reduced delivering operation 216 reduces the selected oxygen concentration immediately to the adjusted oxygen concentration. In alternative embodiments, the ventilator during the reduced delivering operation 216 reduces the selected oxygen concentration gradually until the adjusted oxygen concentration is met, such as in increments of 5%.

If the adjusted oxygen concentration is not equivalent to the regular oxygen concentration, the ventilator during the reduced delivering operation 216 delivers the adjusted oxygen concentration until the set time period expires. Accordingly, in some embodiments, the ventilator during the reduced delivering operation 216 also reduces the set time period. For example, the ventilator during the reduced delivering operation 216 may reduce the set time period by at least 10%, 15%, 30%, 50%, 70%, 75%, 80%, and etc. After the expiration of the set time period and/or the expiration of the reduced time period during the reduced delivering operation 216, the ventilator performs delivering operation 204.

In further embodiments, method 200 includes a display operation (not shown). The ventilator during the display operation displays or illustrates any relevant or beneficial ventilator and/or patient information to the operator and/or patient. For example, the ventilator during the display operation may display at least one of a $SpO_2$ concentration of the patient during delivery of the selected oxygen concentration, the early termination of the selected oxygen concentration, the reduction of a set time period for the selected oxygen concentration, the adjusted oxygen concentration, and/or a predetermined $SpO_2$ threshold. This list is exemplary only and is not meant to be limiting of the invention.

In some embodiments, a microprocessor-based ventilator that accesses a computer-readable medium having computer-executable instructions for performing the method of ventilating a patient with a medical ventilator is disclosed. This method includes repeatedly performing the steps disclosed in method 200 above and/or as illustrated in FIG. 2.

In some embodiments, the ventilator system includes: means for delivering a regular oxygen concentration to a patient during ventilation; means for receiving a user selection of a limited oxygen concentration increase for a set time period; means for delivering a selected oxygen concentration above the regular oxygen concentration based on the received user selection; means for monitoring an oxygen saturation level of blood in the patient during the step of delivering the selected oxygen concentration; means for determining that the oxygen saturation level of the blood exceeds a predetermined threshold prior to expiration of the set time period for the limited oxygen concentration increase; and means for delivering an adjusted oxygen concentration to the patient based on the step of determining

EXAMPLES

Figure 3:
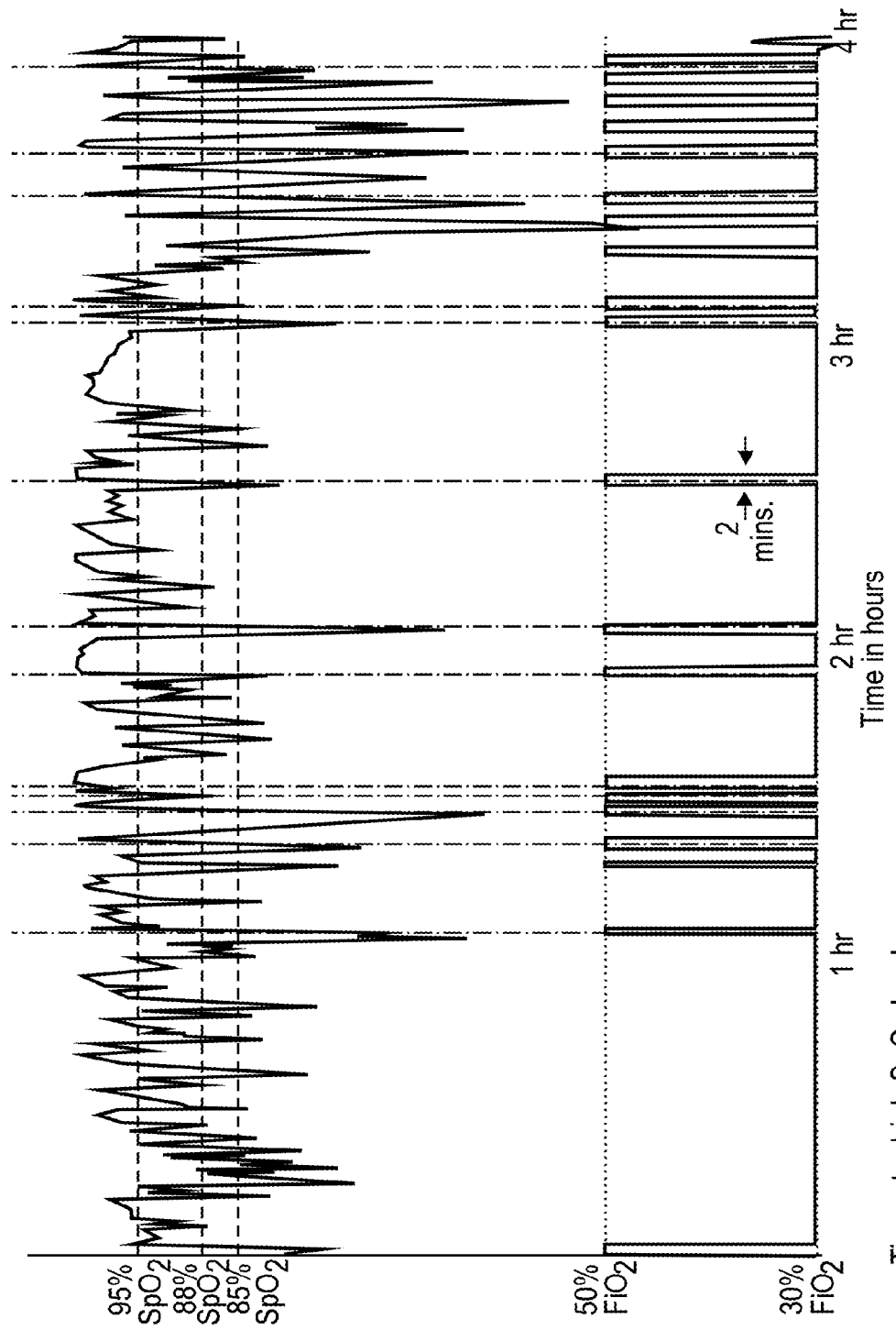
FIG. 3 illustrates an embodiment of a graph of a clinician's use of a 20% increase in $FiO_2$ for two minute intervals in response to episodes of hypoxemia over a 4 hour period of ventilating a patient.

FIG. 3 illustrates an embodiment of a graph of a clinician's use of a 20% increase in $FiO_2$ for two minute intervals in response to episodes of hypoxemia over a 4 hour period of ventilating a patient. The graph and the original data plotted on the graph are from: Nelson Claure, MSc, PhD, Carmen D'Ugard, RRT, and Eduardo Bancalari, MD, Automated Adjustment of Inspired Oxygen in Preterm Infants with Frequent Fluctuations in Oxygenation: A Pilot Clinical Trial, The Journal of Pediatrics 2009;155:640-645. The upper waveform is a plot of the $SpO_2$ level of a patient over a 4 hour period of ventilation. The three different dashed lines indicate $SpO_2$ levels of 85%, 88%, and 95%. The desired range of $SpO_2$ for this patient was from 88% to 95%. A $SpO_2$ level of 85% or below was considered to be too low for the patient. In response to a low $SpO_2$ level, the clinician, operator, or user activated a limited oxygen concentration increase. A $SpO_2$ level above 95% was too large for the ventilation of the patient and placed the patient at risk for developing lung, retinal, and other injuries associated with exposure to elevated levels of oxygen when delivered to the patient.

The bottom waveform on the graph in FIG. 3 shows the regular oxygen concentration from the ventilator, which was set at 30% $FiO_2$. When the user or operator activated the limited oxygen concentration increase, the $FiO_2$ concentration increased from 30% to 50% for the fixed time period of 2 minutes. The horizontal axis is time and covers a span of 4 hours.

Each of the dashed and dotted vertical lines show when the $SpO_2$ level of the patient increased above 95% due to a manual elevation of the oxygen concentration, prior to the two minutes elapsing. During the 4 hour time period, the oxygen concentration was increased 21 times, and in 13 of those, the selected oxygen concentration caused the $SpO_2$ level of the patient to rise above 95%. Accordingly, the patient received too much oxygen 13 times as a result of the manual elevation of oxygen concentration showing the need for systems and methods for preventing and/or reducing the likelihood of a patient from receiving too much oxygen during a selected limited increase in oxygen concentration for a set period of time.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the claims.

What is claimed is:

1. A method for ventilating a patient with a ventilator comprising:
   delivering a regular oxygen concentration to a patient during ventilation;
   receiving a user selection of a limited oxygen concentration increase for a set time period;
   delivering a selected oxygen concentration above the regular oxygen concentration based on the received user selection;
   monitoring an oxygen saturation level of blood in the patient during the step of delivering the selected oxygen concentration;
   determining that the oxygen saturation level of the blood exceeds a predetermined threshold prior to expiration of the set time period for the limited oxygen concentration increase; and
   delivering an adjusted oxygen concentration to the patient based on the step of determining.

2. The method of claim 1, wherein the limited oxygen concentration increase is about a 20% increase in fractional inspired oxygen, and
   wherein the set time period is about two minutes.

3. The method of claim 1, wherein the step of monitoring is performed by an oximeter.

4. The method of claim 1, wherein the patient is selected from a group comprising a preterm infant and an infant.

5. The method of claim 1, wherein the predetermined threshold is one of a group comprising a $SpO_2$ level, a percent increase in $SpO_2$, and an increase in slope of $SpO_2$.

6. The method of claim 1, wherein the predetermined threshold is a 95% oxygen saturation level in the blood of the patient.

7. The method of claim 1, wherein the adjusted oxygen concentration is the regular oxygen concentration.

8. The method of claim 1, wherein the adjusted oxygen concentration reduces the selected oxygen concentration by at least 10%.

9. The method of claim 8, further comprising:
   reducing the set time period by at least 10% based on the step of determining.

10. The method of claim 1, further comprising:
    reducing the set time period by at least 10% based on the step of determining.

11. The method of claim 1, wherein the step of delivering the adjusted oxygen concentration to the patient prevents at least one of lung and retina injury in the patient.

12. The method of claim 1, wherein the step of delivering the adjusted oxygen concentration to the patient gradually reduces the selected oxygen concentration until an oxygen concentration delivered to the patient reaches the adjusted oxygen concentration.

13. The method of claim 1, wherein the step of delivering the adjusted oxygen concentration to the patient immediately reduces the selected oxygen concentration to the adjusted oxygen concentration.

14. The method of claim 1, further comprising:
    displaying at least one of a $SpO_2$ concentration of the patient during the step of delivering the selected oxygen concentration, an early termination of the step of delivering the selected oxygen concentration, a reduced set time period for the limited oxygen concentration increase, the adjusted oxygen concentration, and/or the predetermined threshold.

15. A ventilator system, comprising:
    a user interface;
    an Oxygen Increase Option selectable via the user interface, the Oxygen Increase Option instructs a ventilator system to deliver a selected oxygen concentration above a regular oxygen concentration during ventilation of a patient for a set time period;
    at least one processor; and
    at least one memory, communicatively coupled to the at least one processor and containing instructions for operating the ventilator system after receiving a user selection of the Oxygen Increase Option that, when executed by the at least one processor, perform a method comprising:
       monitoring an oxygen saturation level of blood in the patient;
       determining that the oxygen saturation level of the blood exceeds a predetermined threshold prior to expiration of the set time period; and
       delivering an adjusted oxygen concentration to the patient based on the step of determining.

16. The method of claim 15, wherein the predetermined threshold is one of a group comprising a $SpO_2$ level, a percent increase in $SpO_2$, and an increase in slope of $SpO_2$.

17. The method of claim 15, wherein the adjusted oxygen concentration is the regular oxygen concentration.

18. The method of claim 15, further comprising:
reducing the set time period by at least 10% based on the step of determining.

19. The method of claim 15, wherein the step of delivering the adjusted oxygen concentration to the patient gradually reduces the selected oxygen concentration until an oxygen concentration delivered to the patient reaches the adjusted oxygen concentration.

20. The method of claim 15, further comprising:
displaying at least one of a $SpO_2$ concentration of the patient, a reduced set time period for the Oxygen Increase Option, the adjusted oxygen concentration, and/or the predetermined threshold, and
wherein the user interface is a graphical user interface.

21. A computer-readable medium having computer-executable instructions for performing a method of ventilating a patient with a ventilator, the method comprising:
repeatedly delivering a regular oxygen concentration to a patient during ventilation;
repeatedly receiving a user selection of a limited oxygen concentration increase for a set time period;
repeatedly delivering a selected oxygen concentration above the regular oxygen concentration based on the received user selection;
repeatedly monitoring an oxygen saturation level of blood in the patient during the step of delivering the selected oxygen concentration;
repeatedly determining that the oxygen saturation level of the blood exceeds a predetermined threshold prior to expiration of the set time period for the limited oxygen concentration increase; and
repeatedly delivering an adjusted oxygen concentration to the patient based on the step of determining.

22. A ventilator system, comprising:
means for delivering a regular oxygen concentration to a patient during ventilation;
means for receiving a user selection of a limited oxygen concentration increase for a set time period;
means for delivering a selected oxygen concentration above the regular oxygen concentration based on the received user selection;
means for monitoring an oxygen saturation level of blood in the patient during the step of delivering the selected oxygen concentration;
means for determining that the oxygen saturation level of the blood exceeds a predetermined threshold prior to expiration of the set time period for the limited oxygen concentration increase; and
means for delivering an adjusted oxygen concentration to the patient based on the step of determining.

* * * * *